(12) United States Patent
Phillips

(10) Patent No.: US 6,565,513 B1
(45) Date of Patent: May 20, 2003

(54) ULTRASONIC CARDIAC OUTPUT MONITOR

(75) Inventor: Robert Phillips, Coffs Harbour (AU)

(73) Assignee: Uscom Pty Ltd., Coffs Harbour (GB)

(*) Notice: Subject to any disclaimer, the term of this patent is extended or adjusted under 35 U.S.C. 154(b) by 0 days.

(21) Appl. No.: 09/719,894

(22) PCT Filed: Jun. 23, 1999

(86) PCT No.: PCT/AU99/00507

§ 371 (c)(1), (2), (4) Date: Feb. 12, 2001

(87) PCT Pub. No.: WO99/66835

PCT Pub. Date: Dec. 29, 1999

(30) Foreign Application Priority Data

Jun. 24, 1998 (AU) .............................................. PP 4318

(51) Int. Cl.[7] ................................................. A61B 8/06
(52) U.S. Cl. ...................................................... 600/454
(58) Field of Search ................................ 600/438, 450, 600/443, 447, 453–456

(56) References Cited

U.S. PATENT DOCUMENTS

| | | | | |
|---|---|---|---|---|
| 4,276,885 A | * | 7/1981 | Tickner et al. ............... | 600/458 |
| 4,509,526 A | | 4/1985 | Barnes et al. | |
| 4,926,872 A | * | 5/1990 | Brock-Fisher et al. ......... | 73/626 |
| 5,062,427 A | * | 11/1991 | Seo et al. .................... | 600/447 |
| 5,487,760 A | * | 1/1996 | Villafana ...................... | 623/2 |
| 5,598,845 A | | 2/1997 | Chandraratna et al. | |
| 6,261,231 B1 | * | 7/2001 | Damphousse et al. ...... | 600/437 |

FOREIGN PATENT DOCUMENTS

| | | |
|---|---|---|
| EP | 0 172 687 | 7/1985 |
| WO | WO 89/04634 | 6/1989 |

OTHER PUBLICATIONS

Ihlen et al., "Determination of cardiac output by Doppler echocardiography", 1984, pp. 54–60.

* cited by examiner

Primary Examiner—Francis J. Jaworski
(74) Attorney, Agent, or Firm—Merchant & Gould P.C.

(57) ABSTRACT

A method of cardiac physiologic monitoring is disclosed comprising the steps of: (a) utilizing an external ultrasonic transducer element attached to a patient to determine an information signal indicating of blood floe within a patient's heart; (b) processing the information signal to determine physiologic parameters associated with the heart. The physiologic parameters can include at least one of transaortic peak velocity, mean transvalvular pressure gradient, time velocity integral, stroke volume, cardiac output or any other product as an analogue of output. The method can preferably include monitoring the change in time of the physiologic parameters through continual monitoring of the information signal. The monitoring step preferably can include determining an alarm state if the parameters are preferably outside a predetermined range. The external ultrasonic transducer preferably can include an attached handle operative to position the transducer in a predetermined orientation to the patient's heart.

13 Claims, 7 Drawing Sheets

ULTRASONIC CARDIAC OUTPUT MONITOR

FIELD OF THE INVENTION

The present invention relates to the field of cardiac monitoring and, in particular, discloses a method for utilisation of an external transducer element in ultrasonic cardiac monitoring.

BACKGROUND OF THE INVENTION

The process of accurate cardiac physiologic monitoring is obviously an important process during acute illness and anaesthesia. In particular, early detection of changes in cardiac function can be critical in the reduction of patient morbidity and mortality.

Current methods of direct cardiac monitoring are expensive, technically difficult to operate and provide for variable results.

One common form of monitoring is the electrocardiographic method which monitors the electrical cardiac activity. Unfortunately, this method only provides for an indirect monitoring of cardiac muscle conductivity and not blood flow. Also currently utilised is an ultrasonic method of cardiac physiologic monitoring utilising 2D transoesophageal echocardiographic ventricular transections. However, this method is invasive, expensive and inaccurate by virtue of its technical difficulty and that only 6 of 16 myocardial segments are imaged at any time. Unfortunately, normal left ventricular myocardial function varies transmurally, transtemporally and intersegmentally and the 2D evaluation of the wall motion requires spatial and temporal integration skills only acquired after a programme of extensive and expensive physician training.

There is therefore a general need for an improved, more convenient form of cardiac physiologic monitoring.

SUMMARY OF THE INVENTION

It is an object of the present invention to provide for an improved form of cardiac physiologic monitoring utilising ultrasound techniques.

In accordance with a first aspect of the present invention, there is provided a method of cardiac physiologic monitoring comprising the steps of:
(a) utilising an external ultrasonic transducer element attached to a patient to determine an information signal indicative of blood flow within a patient's heart;
(b) processing the information signal to determine physiologic parameters associated with the heart function.

The physiologic parameters can include at least one of transaortic peak velocity, mean transvalvular pressure gradient, time velocity integral, stroke volume, cardiac output or any other product as an analogue of output.

The method can preferably include monitoring the change in time of the physiologic parameters through continual monitoring of the information signal.

The monitoring step preferably can include determining an alarm state if the parameters are outside a predetermined range.

The external ultrasonic transducer preferably can include an attached handle operative to position the transducer in a predetermined orientation to the patient's heart.

In accordance with a further aspect of the present invention, there is provided a cardiac monitoring system comprising: an external ultrasonic transducer element adapted to be attached to a patient to provide an information signal indicative of blood flow within a patient's heart; computer processing means, interconnected to the transducer element and adapted to process the information signal to determine physiologic parameters associated with the heart.

The physiologic parameters can include at least one of transaortic peak velocity, mean transvalvular pressure gradient, time velocity integral, stroke volume, cardiac output or any other product as an analogue of flow.

BRIEF DESCRIPTION OF THE DRAWINGS

Notwithstanding any other forms which may fall within the scope of the present invention, preferred forms of the invention will now be described, by way of example only, with reference to the accompanying drawings in which.

DESCRIPTION OF PREFERRED AND OTHER EMBODIMENTS

In the preferred embodiment simple Doppler echocardiographic evaluation of cardiac blood flow is utilised to provide accurate and reproducible cardiac output information which allows for the utilization of equipment that is simple in design, durable, inexpensive to manufacture and easy to operate.

In the preferred embodiment, transaortic and transpulmonary continuous wave (CW) Doppler analysis is adapted for use as a heart monitoring device. Continuous wave Doppler is well validated and a routine echocardiographic method of quantitating cardiac output with low inter and intra observer variability.

Figure 1:
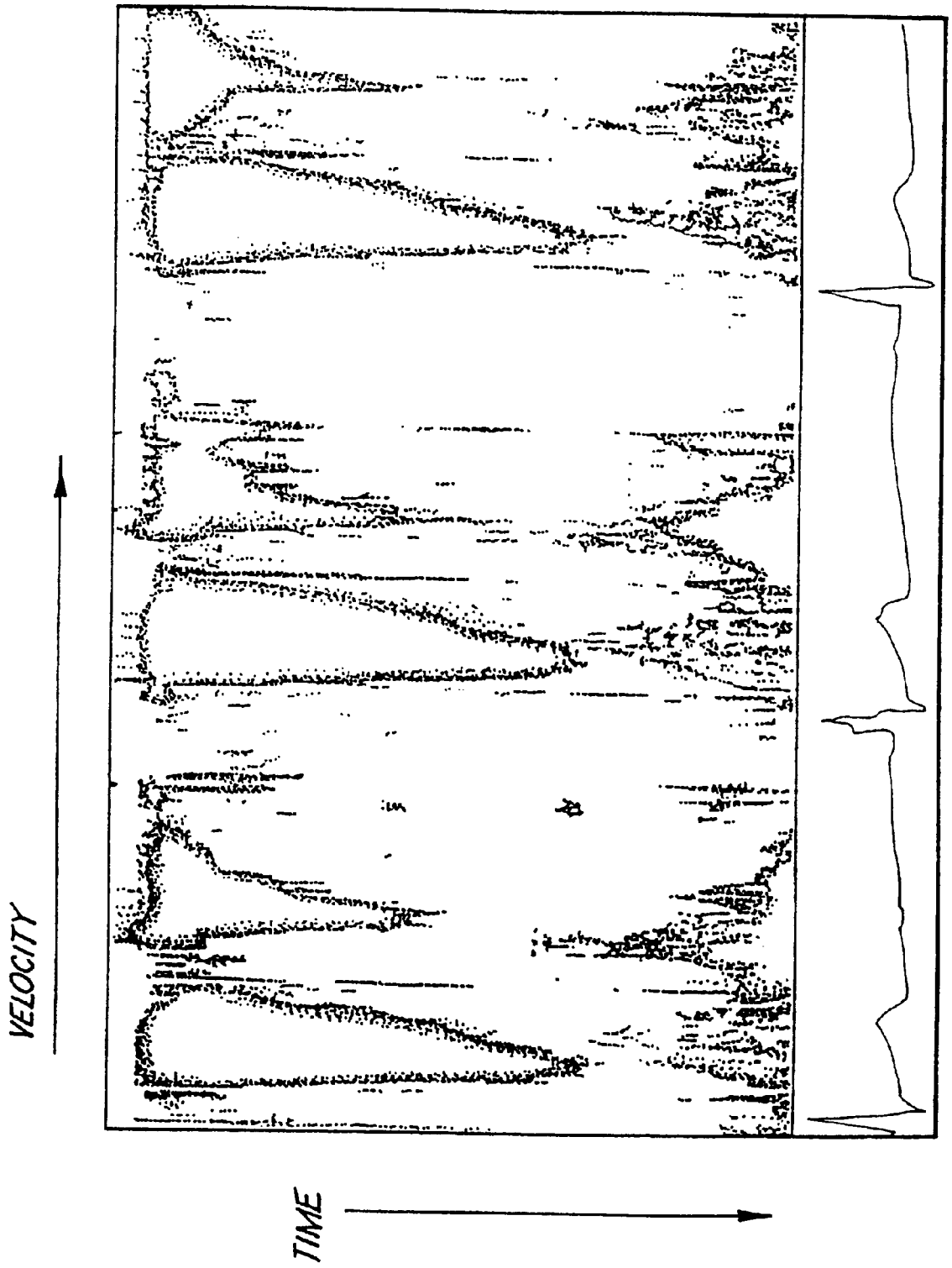
FIG. 1 illustrates an example output of a ventricular insonation.

Turning to FIG. 1, there is illustrated an example CW screen grab output 1 from a 7777 device which provides for a measure of blood velocity over time. The CW method detects the velocity of individual blood cells by measuring the frequency change of a reflected ultrasound beam and displaying this as a time velocity flow profile as indicated in FIG. 1.

Appropriately directed Doppler insonation from the apical or suprasternal acoustic window provides a time velocity profile of transaortic flow, while insonation from the parasternal window provides a transpulmonary flow profile. This flow profile is an analogue of cardiac output and is a real time stroke to stroke measure of cardiac physiology.

Figure 2:
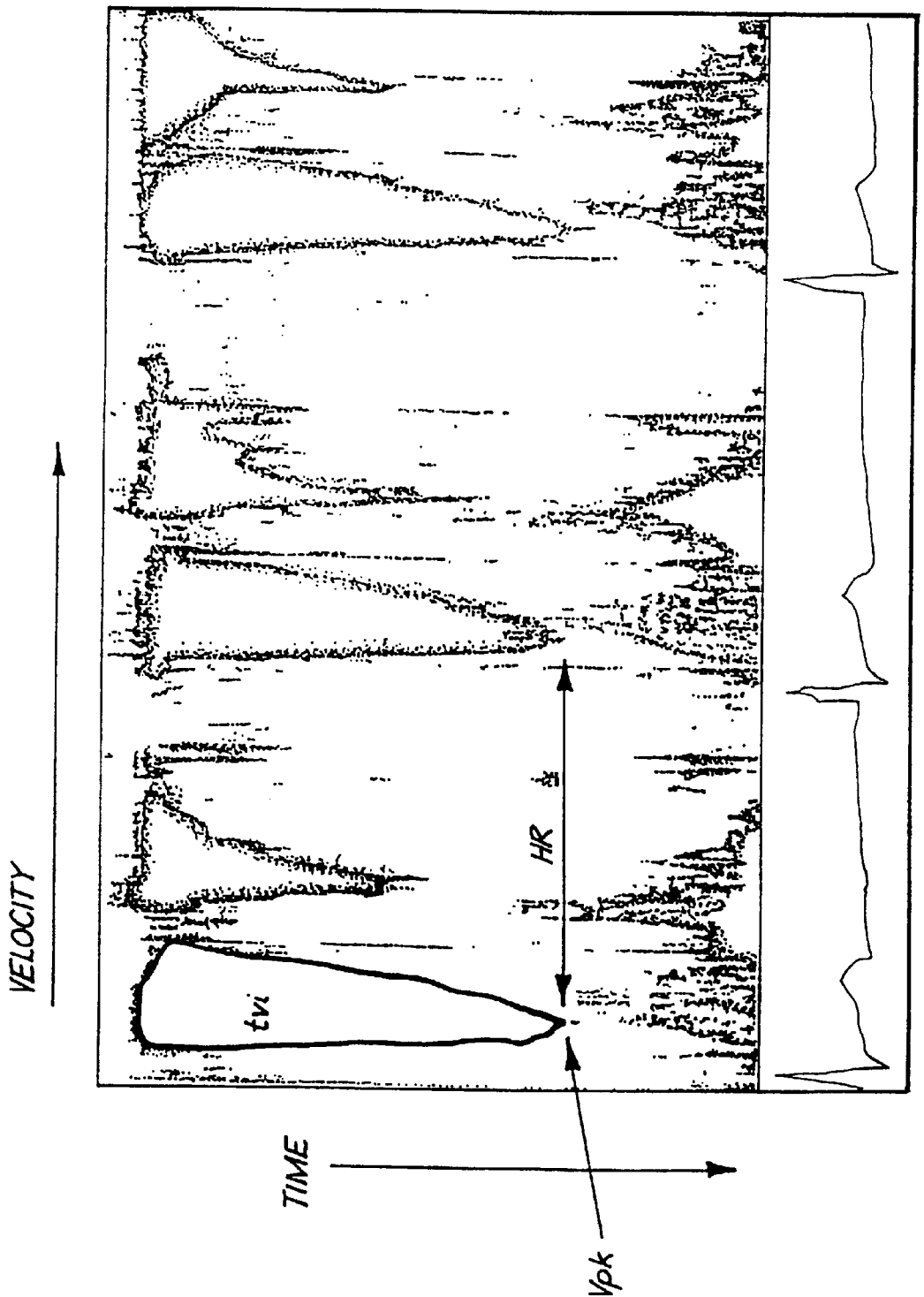
FIGS. 2 and 3 illustrate various features of the output of FIG. 1.

The preferred embodiment utilizes the flow profile to generate a corresponding change monitoring of the flow profile with time. The spectral flow profile can be image processed to be accurately edge detected, providing a real time computed read out of transaortic peak velocity (Vpk) Heart Rate (HR), means transvalvuar pressure gradient (Pmn), tire velocity integral (tvi) and, with a premeasured acrtic (Ao) or pulmonary artery (PA) diameter from a 2D examination, cardiac output (CO) or any other product as an analogue of output can be determined. The measures (Vpk), tvi and HR are illustrated in FIG. 2.

Intracardiac flow across the aortic valve and the pulmonary valve must be equal in the absence of significant regurgitation or trans-septal flow (shunt), and regardless, both can be used to reflect changes in cardiac output, so the choice of whether transpulmonary or transaortic monitoring is chosen can depend only on the ease of signal access.

Although absolute flow can be determined using aortic valve or pulmonary artery diameter derived from a 2D echocardiogram, this may not be required as the relevance of physiologic monitoring is dependent on detecting temporal changes in output. Therefore, a change from either the baseline transoartic or transpulmonary profile would, providing there was no significant change in the angle of insonation, represent a change in output proportional to the change in the baseline parameters (tvi, Pmn, Vpk and CO) etc.

Figure 3:
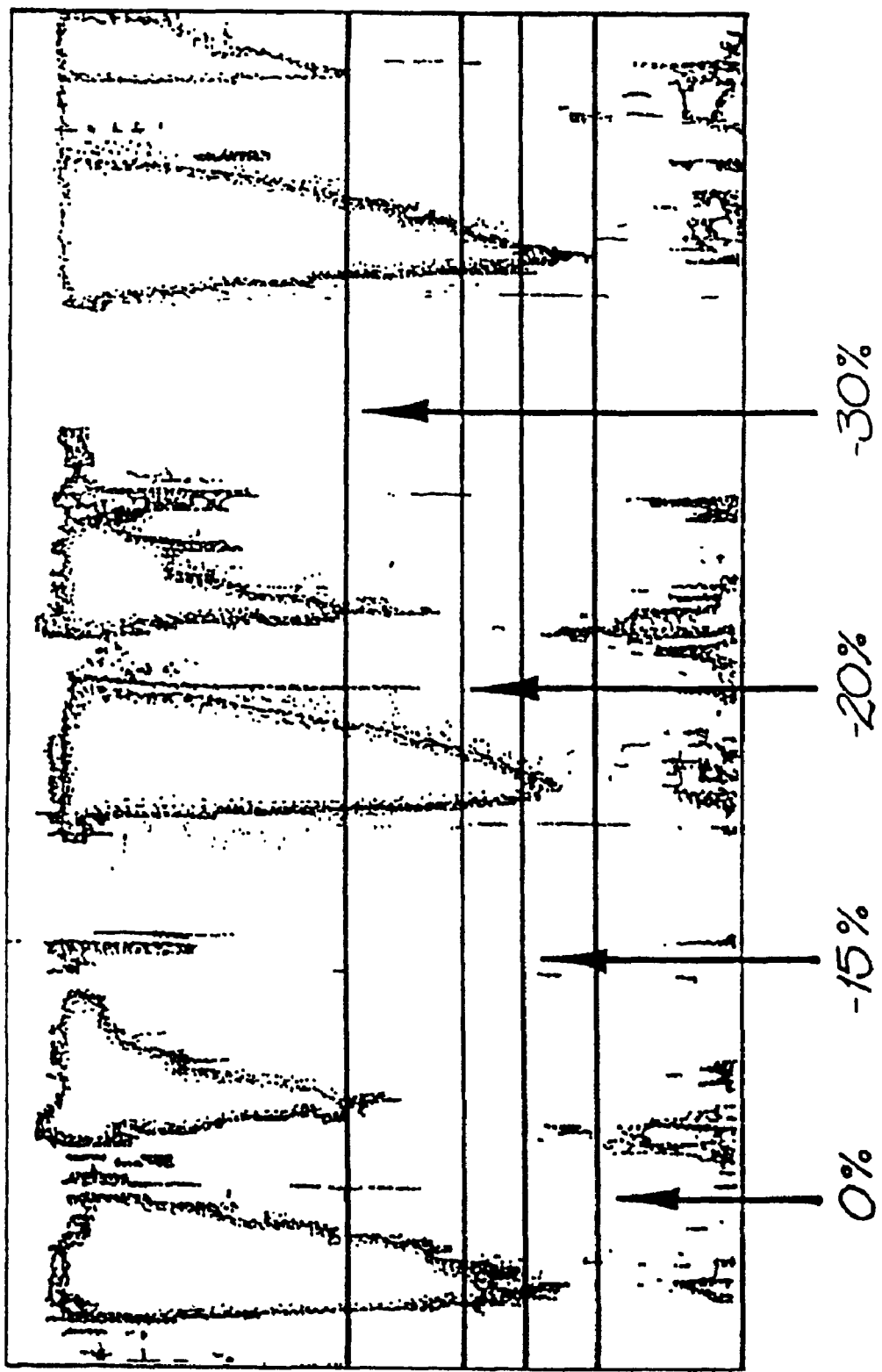

In the preferred embodiment normal variance ranges for haemodynamic parameters can be preferably user selected from the reference cycles so that an alarm would sound if signals exceeded this range. As illustrated in FIG. 3, the tolerance for alarm activation for (Vpk) could be a stepped user selected variable set to compensate for individual baseline stroke to stroke variability (−15%, −20%, −30% etc).

Arrhythmias are associated with cardiac disease and can produce high stroke to stroke variability of haemodynamic parameters making automated single cycle signal analysis unrepresentative. This can be addressed using multi cycle signal averaging so that a user selected variable number of cycles would be averaged to give mean Vpk, Pmn, tvi and CO parameters for alarm detection and the setting of wide alarm parameters for stroke to stroke variability.

The direct measurement of transpulmonary flow can be achieved by applying a small CW transducer with an adherent gel coupling layer to the surface of the skin at the left parasternal acoustic window; adjacent to the sternum in an intercostal interspace, while the transaortic flow can be detected from the intercostal space associated with the palpable ventricular apex beat or from the suprasternal notch. The transducer can be fixed in place with adhesive tape or sheet and or a transthoracic belt utilising a thin gel coupling layer to ensure transducer skin contact.

Figure 4:
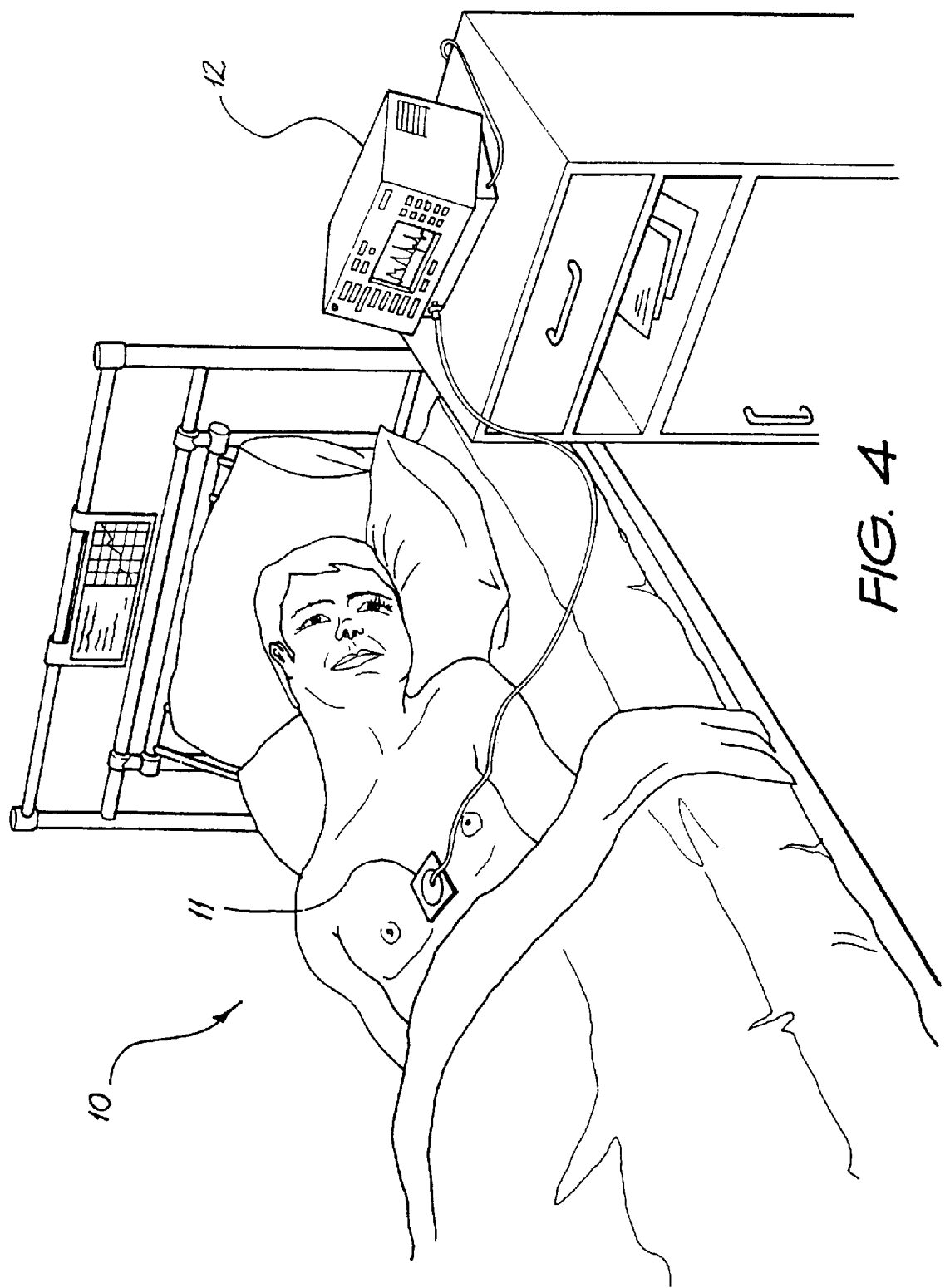
FIG. 4 is a perspective view of an arrangement of the preferred embodiment when utilised to monitor a patient.

In FIG. 4 there is illustrated an example arrangement with a patient 10 being monitored utilising a transducer element 11 interconnected with a computer signal processing unit 12.

Figure 5:
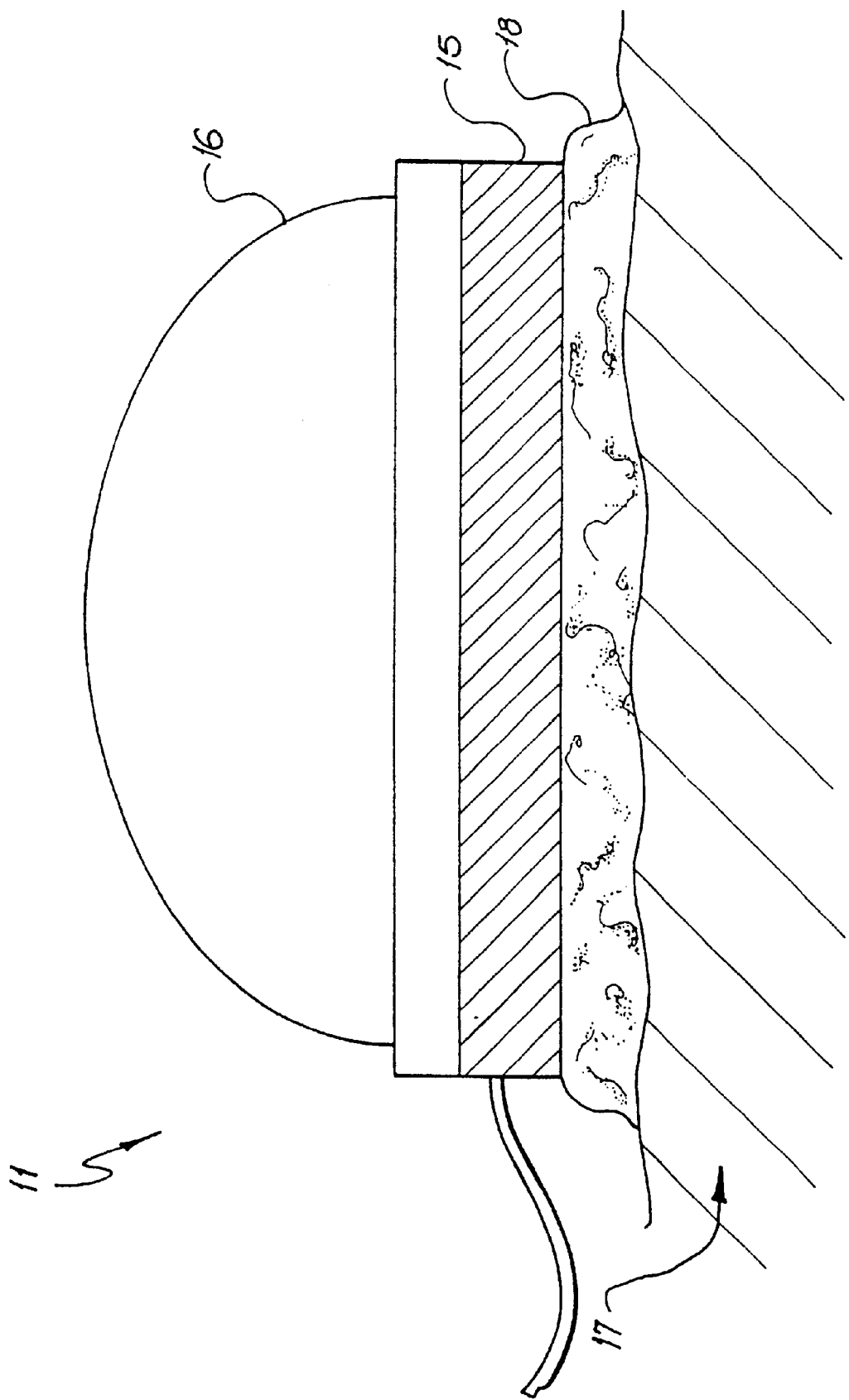
FIG. 5 illustrates a sectional view of the transducer element.

In FIG. 5, there is illustrated an enlarged sectional view of the transducer element 11 which includes a transducer 15 attached to a positioning device 16 which can be utilised to initially set the position of the transducer. Between the transducer 15 and a person's skin 17 is placed a gel coupling layer 18 for coupling the ultrasonic transducer vibrations to the skin 17.

Figure 6:
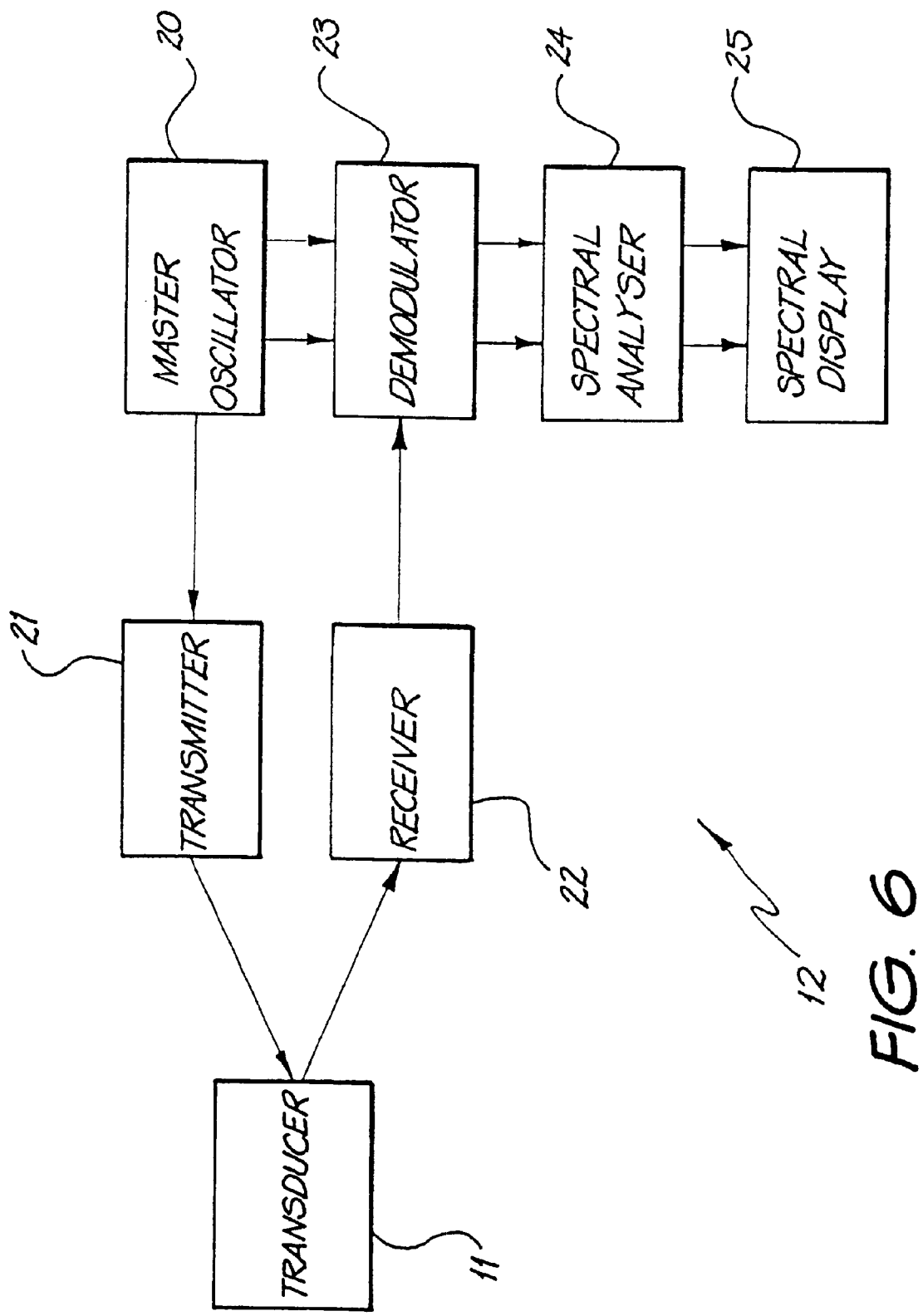
FIG. 6 is a functional block diagram of the preferred embodiment.

Turning now to FIG. 6, there is illustrated, in functional block diagram form, one form of construction of the computer system 12 of FIG. 4. The system 12 includes a master oscillator 20 which is interconnected to a transmitter 21 which is responsible for transmitting the oscillation to transducer 11. The transducer 11 includes receiver 22 which is forwarded to a demodulating element 23 which utilises phase outputs from the master oscillator 20 so as to demodulate the received signal from receiver 22 so as to provide for a spectral output which is forwarded to a spectral analyser 24 which can in turn include a computer digital signal processor arrangement for processing the output signal so as to determine the relevant parameters. The spectral analyser 24 can comprise a computer type device with appropriate DSP hardware. The spectral analyser 24 outputs to a spectral display 25 which can include a standard user interface of relevant information. For example, in FIG. 7, there is shown an example display output which includes buttons for setting various sensitivity and alarm ranges so as to provide for full cardiac physiologic monitoring.

The continuous wave ultrasound transducer (1.0 to 3.0 Mhz) 11 can include a small raised toggle for angular adjustment. The transducer can be strapped to the left ventricular apical intercostal window, the left parasternal intercostal window or the suprasternal notch and fixed in place wrath an adhesive sheet or tape, and a belt.

Figure 7:
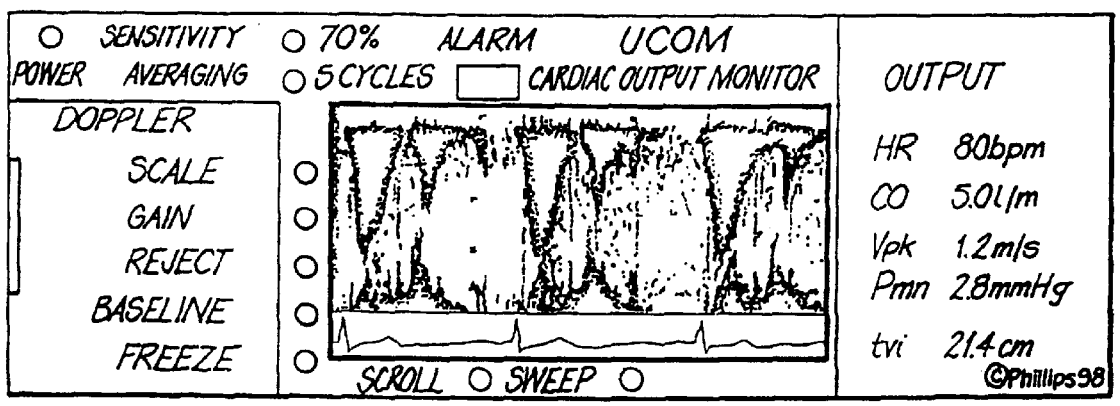
FIG. 7 illustrates an example form of user interface suitable for use with the preferred embodiment.

Turning now to FIG. 7, there is illustrated the steps involved in the method of requisite features extraction by the DSP processor. The steps 30 rely on standard image processing techniques well known to those skilled in the art of computer image processing.

Initially, a first CW image is captured 31. From this image, the edges are extracted 32 and analyzed so as to determine the relevant perameters 33, By repeating the process 31–33 for multiple frames, it is possible to determine variations in time base perameters 34. These variations can be saved 35 or output 36 for display and monitoring.

Obviously, many different arrangements of a system are possible. The system could be utilised as a stand alone physiologic monitor, integrated with oximetry, ECG etc or to provide for a remote monitor with on-board analysis or remote transmission.

It would be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. A method of cardiac physiological monitoring of a patient, comprising the steps of:
   (a) utilizing a transcutaneous ultrasonic transducer element attached to the patient to monitor directly the transvalvular cardiac flow of fluid through the cardiac valves of the patient's heart and to generate an information signal indicative of fluid flow within the patient's heart;
   (b) processing said information signal to determine one or more physiological parameters associated with the heart.

2. A method as claimed in claim 1 external ultrasonic transducer element monitors the flow within the heart from the patient's chest using the parasternal or apical thoracic acoustic access.

3. A method as claimed in claim 1 wherein said physiological parameters include as least one of transaortic peak velocity, mean transvalvular pressure gradient, time velocity integral, stroke volume or cardiac output.

4. A method as claimed in claim 1 further comprising the step:
   (c) monitoring the change with time of said physiological parameters through continual monitoring of said information signal.

5. A method as claimed in claim 1 wherein said monitoring step includes determining an alarm state if said parameters are outside a predetermined range.

6. A method as claimed in claim 1 wherein said external ultrasonic transducer includes an attached handle operative to position said transducer in a predetermined orientation to said patient's heart.

7. The method of claim 1 wherein the fluid is blood.

8. A cardiac monitoring system for use with a patient, comprising:

a transcutaneous ultrasonic transducer element adapted to be attached to the patient and to monitor directly the transvalvular cardiac flow of fluid flowing through cardiac valves of the patient's heart and to thereby provide an information signal indicative of fluid flow within the patient's heart, computer processing means interconnected to said transducer element and adapted to process said information signal to determine one or more physiological parameters associated with the heart.

9. A cardiac monitoring system as claimed in claim 8 wherein said external ultrasonic transducer element is adjusted to be affixed to a parasternal or apical thoracic acoustic access point.

10. A cardiac monitoring system as claimed in claim 8 wherein said physiological parameters include at least one of transaortic peak velocity, mean transvalvular pressure gradient, time velocity integral, stroke volume or cardiac output.

11. A cardiac monitoring system as claimed in claim 8 further comprising:

alarm means interconnected to said computer processing means and adapted to emit an alarm if said parameters are outside a predetermined range.

12. A cardiac monitoring system as claimed in claim 8 wherein said external ultrasonic transducer element includes an attached handle operative to position said transducer in a predetermined orientation to said patient's heart.

13. The system of claim 8 wherein the fluid is blood.

* * * * *